United States Patent
Reuter et al.

(10) Patent No.: US 12,257,179 B2
(45) Date of Patent: Mar. 25, 2025

(54) COUPLABLE PORTABLE DEVICE FOR THE THERMAL MEDICAL TREATMENT OF SKIN

(71) Applicant: KAMEDI GMBH, Eggenstein-Leopoldshafen (DE)

(72) Inventors: Christof Reuter, Friesheim (DE); Stefan Hotz, Muehlhausen (DE); Armin Meyer, Berlin (DE); Lukas Heinrich Liedtke, Korbach (DE)

(73) Assignee: KAMEDI GMBH, Karlsruhe (DE)

( * ) Notice: Subject to any disclaimer, the term of this patent is extended or adjusted under 35 U.S.C. 154(b) by 0 days.

(21) Appl. No.: 18/617,690

(22) Filed: Mar. 27, 2024

(65) Prior Publication Data

US 2024/0238116 A1   Jul. 18, 2024

Related U.S. Application Data

(63) Continuation of application No. 16/623,839, filed as application No. PCT/DE2018/100644 on Jul. 13, 2018, now abandoned.

(30) Foreign Application Priority Data

Jul. 24, 2017   (DE) ..................... 10 2017 006 994.8

(51) Int. Cl.
*A61F 7/00*   (2006.01)
*A61F 7/02*   (2006.01)

(52) U.S. Cl.
CPC ...... *A61F 7/007* (2013.01); *A61F 2007/0052* (2013.01); *A61F 2007/0071* (2013.01);
(Continued)

(58) Field of Classification Search
CPC .............. A61F 2007/0052; A61F 7/007; A61F 2007/0071; A61F 2007/0077;
(Continued)

(56) References Cited

U.S. PATENT DOCUMENTS 7,537,605 B2    5/2009  Li et al.
7,637,930 B2   12/2009  Li et al.
(Continued)

FOREIGN PATENT DOCUMENTS

CN    201799014 U    4/2011
CN    102429762 A    5/2012
(Continued)

OTHER PUBLICATIONS

International Search Report in PCT/DE2018/100644, mailed Dec. 12, 2018.

*Primary Examiner* — Kaitlyn E Smith
*Assistant Examiner* — Bradford C. Blaise
(74) *Attorney, Agent, or Firm* — Collard & Roe, P.C.

(57) ABSTRACT

A portable device for the thermal medical treatment of skin allows a treatment attachment to be coupled to a mobile data-processing unit, preferably a smartphone or a tablet, via an interface, wherein a housing of the treatment attachment which extends over the treatment attachment is provided with a heating element directly underneath the surface facing away from the data-processing unit in the coupled state, the heating element being coupled to a temperature sensor, wherein the heating element, with the interposition of a control unit, is connected to the electrically conductive interface or, via a Bluetooth connection, to the data-processing unit in such a way that the heating element is supplied with power via one or more rechargeable batteries integrated into the data-processing unit in such a way that the heating element can be heated to a temperature predefined via the control unit.

15 Claims, 2 Drawing Sheets

(52) U.S. Cl.
CPC . *A61F 2007/008* (2013.01); *A61F 2007/0086* (2013.01); *A61F 2007/0087* (2013.01); *A61F 2007/0282* (2013.01)

(58) Field of Classification Search
CPC ........ A61F 2007/0078; A61F 2007/008; A61F 2007/0086; A61F 2007/0087; A61F 2007/0088; A61F 2007/0093; A61F 2007/0094; A61F 2007/0095; A61F 2007/0096; A61F 2007/0282; A61F 2007/0284; A61F 2007/0225; A61F 2007/0228; A61F 2007/0233
See application file for complete search history.

(56) References Cited

U.S. PATENT DOCUMENTS

| | | |
|---|---|---|
| 8,658,943 B1 | 2/2014 | Larsen et al. |
| 8,907,251 B2 | 12/2014 | Larsen et al. |
| 9,844,459 B2 | 12/2017 | Badawi |
| 2009/0240297 A1 | 9/2009 | Shavit et al. |
| 2010/0179623 A1 | 7/2010 | Hofer et al. |
| 2013/0172829 A1 | 7/2013 | Badawi |
| 2014/0200487 A1 | 7/2014 | Ramdas et al. |
| 2014/0330336 A1 | 11/2014 | Errico et al. |
| 2016/0324719 A1 | 11/2016 | Badmus et al. |
| 2016/0331993 A1 | 11/2016 | Moyer |
| 2017/0079834 A1 | 3/2017 | Badawi |
| 2017/0172227 A1 | 6/2017 | Fan et al. |
| 2017/0290980 A1 | 10/2017 | Friedli et al. |
| 2018/0094983 A1 | 4/2018 | Tierney et al. |
| 2018/0153399 A1 | 6/2018 | Fink et al. |
| 2019/0290477 A1 | 9/2019 | Buenger |
| 2020/0044318 A1 | 2/2020 | Pilla et al. |

FOREIGN PATENT DOCUMENTS

| | | |
|---|---|---|
| CN | 104334129 A | 2/2015 |
| CN | 106102667 A | 11/2016 |
| DE | 199 54 424 A1 | 6/2001 |
| DE | 101 34 878 A1 | 2/2003 |
| DE | 20 2012 100 037 U1 | 2/2012 |
| DE | 20 2014 104 077 U1 | 9/2014 |
| DE | 10 2014 105 631 A1 | 10/2014 |
| DE | 10 2016 013 448 A1 | 6/2017 |
| EP | 1 231 875 B1 | 9/2004 |
| JP | 3025336 U | 6/1996 |
| KR | 20110092630 A | 8/2011 |
| KR | 10-1722904 B1 | 4/2017 |
| WO | 2007/082648 A1 | 7/2007 |
| WO | 2015/109397 A1 | 7/2015 |
| WO | 2016/041863 A1 | 3/2016 |

COUPLABLE PORTABLE DEVICE FOR THE THERMAL MEDICAL TREATMENT OF SKIN

CROSS REFERENCE TO RELATED APPLICATIONS

This application is a Continuation Application and Applicant claims priority under 35 U.S.C. § 120 of U.S. patent application Ser. No. 16/623,839, now abandoned, which was filed on Dec. 18, 2019, which application is a national stage application under 35 U.S.C. § 371 of PCT Application No. PCT/DE2018/100644 filed on Jul. 13, 2018, which claims priority under 35 U.S.C. § 119 of German Application No. 10 2017 006 994.8 filed on Jul. 24, 2017, the disclosure of which is incorporated by reference. The international application under PCT article 21 (2) was not published in English.

1. FIELD OF THE INVENTION

The invention relates to a couplable device for the thermal-medical treatment of skin, in particular in the case of skin irritations or minor injuries as can be induced, for example, by insect bites or plants.

2. DESCRIPTION OF THE RELATED ART

A device for the local thermal treatment of insect bites is already known in this context from EP 1 231 875 B1, which is capable of acting on the affected skin region using a heat treatment. Specifically, this device is equipped with a heating element, which is embodied as an electrical heating plate and is powered by a voltage source (not specified in greater detail). In this case, the temperature of the heating plate is limited to a highest temperature of 50-65°, preferably of 55° to 60°, to avoid possible burns. Moreover, this temperature is only maintained for a time frame of a few seconds. To ensure this, the heating element is provided with a temperature sensor and with a control unit in order to control the corresponding heat treatment, in particular the temperature used and the duration of the mentioned treatment according to the above-explained specifications. In practice, however, it is rather impractical to carry along a heating plate in conjunction with outdoor activities.

In the case of the above-mentioned skin irritations, it has been shown that the effectiveness of the mentioned heat treatment is also dependent, inter alia, on the mentioned heat treatment being carried out as rapidly as possible. However, because the mentioned skin irritations are primarily caused by insect bites, plants, or also fish, algae, or jellyfish or other cnidarians, thus frequently in the so-called outdoor area, it is advisable to carry out the mentioned heat treatment as rapidly as possible, i.e., best directly on location. It is self-evident that the most compact possible solution enables continuous carrying along and thus a timely treatment.

Moreover, a method for treating dry eyes is known from US 2017/0079834 A1, in which heatable strips are applied above and below the human eye, which are each connected via current-conducting cables to a programmable control unit, which controls the further treatment of the mentioned eye parts. This control unit is additionally connected to a portable electronic device, for example, a smart phone or a tablet. The power supply of the heatable strips is performed, however, via the control unit, so that a suitable energy accumulator also has to be integrated into this control unit.

A portable device for treating external boils, i.e., swelling of the human body, is previously known from WO 2015/109397 A1, which also teaches acting on the affected body parts using heated strips or compresses. A heat treatment is also carried out here, wherein it is also expected here of the user that he carries along a comparatively voluminous portable unit for the case of a corresponding injury to be able to treat the mentioned body swelling in an emergency.

Finally, a portable item of clothing is known from US 2017/017 2227, in particular for clothing the upper body, in which so-called micro-tubes are incorporated, wherein each of these tubes is provided with an inlet and an outlet, so that it is possible to conduct heated or cooled air through these micro-tubes to provide cooling or heating to the user. Moreover, this piece of clothing is provided with an environmental sensor for detecting the ambient temperature, so that an automatic regulation is possible in dependence on the ambient temperature and the presets presumably selected by the user. This thus relates to a temperature control of the human body, in particular the upper body, but not to a treatment of possible skin irritations.

Moreover, devices are already known which can alleviate the itching and the swelling of insect bites in a targeted manner by means of concentrated heat and a micro-electrical controller (EP 1231875, CN102429762A, US000007537605B2, US000007637930B2, DE202012100037, DE202014104077U1, WO2007/082648, DE 000019954424 A1). All above devices share the feature that they function independently and are provided with a housing which is also required for handling the previously known devices during the heat treatment. None of the cited devices is Internet-capable or otherwise networked.

As a result, all previously known devices thus appear unsuitable for physically active outdoor use, for example, for types of sports such as free climbing or mountain biking or also longer bicycle tours or hikes, in which the baggage carried along is generally limited, because they cannot be reasonably carried along as a result of the weight and the size thereof. This also applies to carrying them along continuously in everyday use.

SUMMARY OF THE INVENTION

Proceeding from this prior art, the invention is based on the object of providing a portable device, which can be carried along easily in a space-saving and weight-saving manner and rapidly provides an initial alleviation or even a complete remedy in conjunction with the mentioned skin irritations.

This object is achieved by means of a portable device disclosed herein. Advantageous designs of the invention are also disclosed.

The invention relates to a portable device for the thermal-medical treatment of the skin, as is performed, for example, in conjunction with insect bites or other skin irritations. In this case, the device according to the invention essentially consists of a small-format treatment attachment, which is only a few centimeters wide and long and can thus be carried along without problems in the trouser pocket, for example.

The treatment attachment essentially consists of a housing and is equipped on the lower side with an interface for coupling to a mobile data processing unit. The treatment attachment both has a data connection to the mobile data processing unit and also is supplied with electrical energy via this interface. Due to the external power supply, the energy accumulator typically integrated into the mobile data processing unit can be used to energize a suitably arranged heating element. The surface thus heated can be placed by corresponding handling of the connected data processing unit onto the skin surface to be treated, so that it is subjected to a heat treatment in a preferred range between 50° and 65°.

This thermal treatment is used to alleviate the itching and for a more favorable course of healing, relating to the treatment of insect bites, snake venom, or urticants, as are transferred, for example, from plants or animals, such as jellyfish. The device according to the invention can additionally be used for treating herpes or other skin diseases.

For example, introduced toxicants are decomposed and the healing process is accelerated as a whole by the heat treatment. In this case, the course of treatment can be displayed and followed on the data processing unit via the data connection. The risk of possible infections, for example, as a result of insect bites or tick bites, is also reduced in this way.

In the coupled state, the handling of the small-format treatment attachment is facilitated in that the typically larger-area data processing unit can be used to place the treatment attachment as intended on the skin part to be treated.

In a specific design, a heating element, which is generally implemented by a resistor which heats up upon energizing, is arranged in the housing of the treatment attachment directly below the surface of the treatment attachment facing away from the data processing unit in the coupled state. A temperature sensor, via which the ambient temperature of the resistor is detected, is arranged directly adjacent to this heating element.

In a further design, the temperature sensor has a data connection via the interface to the mobile data processing unit, so that the temperature of the resistor can be controlled and/or regulated via suitable software.

In this case, both the mentioned heating element and also the temperature sensor are connected to the mobile data processing unit via the above-mentioned interface with a microcontroller interconnected. The control or regulation of the temperature of the resistor is performed in this case via the mentioned microcontroller and therefore if necessary independently of the mobile data processing unit. In this case, the heating element and the temperature sensor can be combined in a single component.

In one advantageous design of the invention, the interface is used not only for the power supply of the resistor employed for the heat treatment, but rather also for the data connection to the mobile data processing unit. In this way, further items of information, for example, relating to the course of treatment, can be transmitted to the data processing unit and stored therein. Moreover, the obtained data can also be used to obtain items of information about potential insect plagues, and also the spread of insects or illnesses.

In another advantageous design of the invention, the treatment attachment itself can also already be provided with a small energy accumulator, so that the treatment attachment as such is usable for an at least initial alleviating treatment if necessary, for example, if a data processing unit is not available or the data processing unit is not itself functional. Under these circumstances, the treatment attachment can optionally also be used as a stand-alone device.

The data obtained in conjunction with this treatment can be transmitted, for example, wirelessly via the microcontroller, i.e., for example, via Bluetooth, to the data processing unit.

To enable the universal usage of the treatment attachment, the interface is provided with the conventional connectors for connection to typical data processing units, i.e., for example, a lightning or USB connector. In principle, a wireless connection is also possible, for example, via Bluetooth or induction. The attachment is thus usable in conjunction with all commercially available mobile data processing units.

In one advantageous design, the invention is embodied as water-resistant or even watertight to enable the usage under difficult circumstances, i.e., for example, in rain, and hygienic cleaning.

In another advantageous design, the mobile data processing unit is equipped with software, which can be used for operating and controlling the treatment attachment. To improve the functionality and the treatment carried out by means of the treatment attachment, for example, the user can store individual parameters, such as an application case, affected body region, age, sensitivity, or relevant illnesses in the software, so that the treatment can be controlled and/or regulated in consideration of these parameters.

Furthermore, the software can be used to make an emergency call in conjunction with a location specification, for example, upon the occurrence of defined events, i.e., for example, if no further activity or movement of the user of the device according to the invention can be established after a defined time after the treatment.

The invention is explained in greater detail hereafter on the basis of an exemplary embodiment.

DETAILED DESCRIPTION OF PREFERRED EMBODIMENTS

Figure 1:
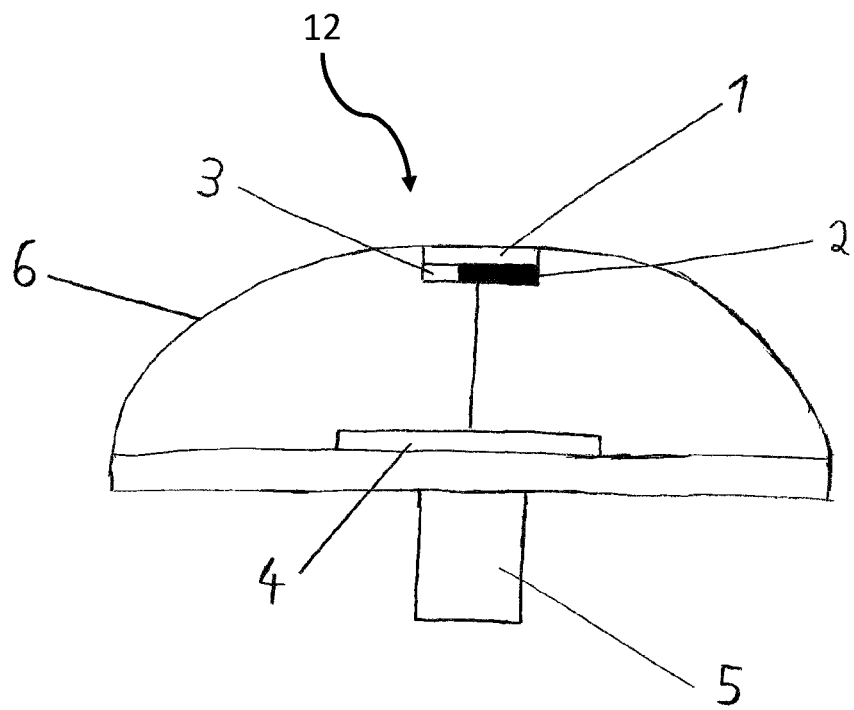
FIG. 1: shows a treatment attachment in a cross-sectional view.

According to the illustration in FIG. 1, the treatment attachment comprises a housing 6, under which an interface 5 extends for connection to a mobile data processing unit 7 (not shown in this figure). A heating element 2, in the immediate vicinity of which a temperature sensor 3 is additionally arranged, is arranged inside the housing 6 directly below the surface of the housing 6 facing away from the interface 5. As soon as the heating element 2 is energized, the surface of the housing 6 facing away from the interface 5 is accordingly heated, so that a heat treatment is executable using this heated section of the surface of the housing 6. The power supply of the heating element 2 takes place via an electrically conductive connection, which is connected by the interface 5 to the heating element 2 with a microcontroller 9 interconnected.

DETAILED DESCRIPTION OF PREFERRED EMBODIMENTS

Figure 2:
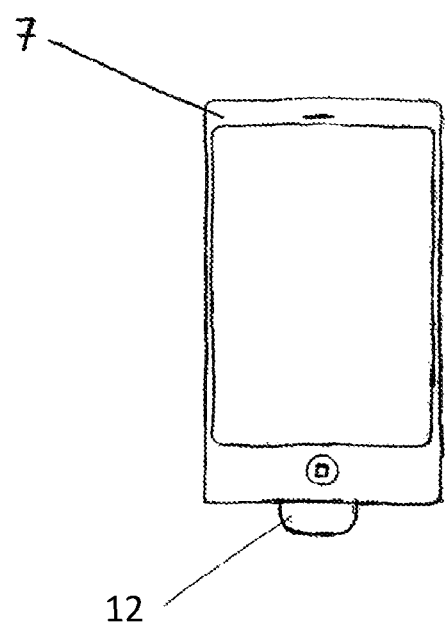
FIG. 2: shows a mobile data processing unit having connected treatment attachment.

FIG. 2 shows the treatment attachment 12 illustrated in FIG. 1 in direct contact with the mobile data processing unit 7, specifically in which the interface 5 is completely inserted into a suitable connector opening, i.e., for example, a lightning or USB connector of the mobile data processing unit 7, so that the treatment attachment 12 is directly connected to the data processing unit 7. In this case, the power and data supply of the heating element 2 and the microcontroller 4, and also of the temperature sensor 3 associated with the heating element, takes place via the interface 5.

As is also apparent from this figure, the treatment attachment 12 protrudes only slightly beyond the data processing unit 7 in the coupled position, so that, for the treatment of a skin irritation, the mobile data processing unit 7 is used at the same time for handling the treatment attachment 12, i.e., predominantly for the purpose of placing the surface of the treatment attachment 12 facing away from the mobile data processing unit 7 on the affected skin part for the purpose of the heat treatment.

Figure 3:
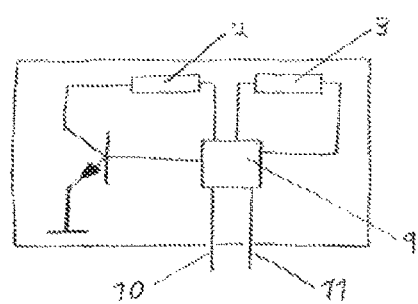
FIG. 3: shows a block diagram of the function of the treatment attachment according to FIG. 1.

FIG. 3 shows a block diagram in simplified form, relating to the circuit arranged inside the treatment attachment 12. Firstly, this circuit shows that, via the interface 5, the circuit arranged in the housing is connected to the connected data processing unit 7 via a power supply 10, and via a data line 11 to the data processing unit 7.

In one specific design, the heating element 2 is a resistor. Both the temperature sensor 3 and also the heating element 2 are connected to the data processing unit 7 in this case with a microcontroller 9 interconnected.

It is not shown in the figure, but it is nonetheless possible and/or provided in the scope of the invention that a mobile application, i.e., in particular an app, which primarily permits the heating procedure to be started and suitable parameters to be specified, is installed on the data processing unit 7. The heating element 2 is then activated in dependence on these settings, wherein the procedure is controlled via the microcontroller 9, which moreover transmits defined data for visualizing and monitoring the treatment procedure to the mobile application installed on the data processing unit 7.

The microcontroller 9 is typically implemented as a component of the control unit 4, wherein the control unit 4 is typically additionally provided with a transistor circuit for the power regulation of the heating element.

Thus, for example, reaching a predetermined temperature or ending the treatment procedure can be transmitted to the data processing unit 7.

The temperature sensor which is also integrated into the housing 6 consists in one advantageous design of two sensors which are not thermally coupled to one another, wherein one sensor measures the temperature of the heating element, while the second sensor detects the skin temperature. The healing process can be accurately monitored and controlled on the basis of this arrangement.

The connection of the treatment attachment 12 to the mobile data processing unit, in particular in conjunction with the mobile application which is also installed on the data processing unit 7, enables the treatment procedure to be improved in that the mobile application is firstly equipped with data by the user himself, for example, relating to the health state of the user, which can then also be taken into consideration during the application of the treatment attachment 12. Moreover, the monitoring of the treatment process by the mobile application can also be used to make an emergency call if necessary, specifically, the parameters stored in the control unit 4 would be met, for example, if no further movement of the user occurs or other parameters make an emergency situation probable. In these cases, an emergency call with specification of the potential location of the user can be placed automatically via the mobile application.

A portable device for the treatment of skin irritations or small injuries, such as insect bites, effects of stinging plants or cnidarians, is thus described above, which is designed in a very small format and can therefore be carried along easily. Only a connector on a mobile data processing unit, which is typically currently carried along by everyone, is required to use the treatment attachment 12.

LIST OF REFERENCE SIGNS

1 coupling unit
2 heating element
3 temperature sensor
4 control unit
5 interface to a digital data processing unit
6 housing
7 mobile data processing unit
9 microcontroller
10 data line
11 power supply
12 treatment attachment

We claim:

1. A portable device for thermal-medical treatment of the skin, comprising:
   a housing that is provided with a heating element and a temperature sensor:
   an interface via which the portable device is coupled to a mobile data processing unit, comprising at least one of a smartphone and a tablet, the interface formed as a rigid extension of a body of the housing; and
   a control unit,
   wherein the heating element is coupled to the temperature sensor and, with the control unit interconnected, is connected via the interface to the mobile data processing unit so that the heating element is supplied with current via one or more rechargeable batteries integrated into the mobile data processing unit so that the heating element is heatable to a temperature controllable by the control unit;
   wherein the portable device in a coupled state is attached directly to the mobile data processing unit via insertion of the interface of the housing into a connector opening of the mobile data processing unit to form a rigid coupling therebetween that enables the mobile data processing unit to act as a handle for the portable device, and is adapted so that for the purpose of treatment of the skin, a surface of the housing facing away from the mobile data processing unit, under which the heating element is arranged within the housing, is placed by corresponding handling of the mobile data processing unit on a body part to be treated.

2. The portable device according to claim 1, wherein the heating element comprises a resistor which heats up upon energizing, wherein the heating element is arranged within the housing directly adjacent to the temperature sensor directly below the surface of the housing of the portable device facing away from the mobile data processing unit in the coupled state, wherein both the temperature sensor and the resistor are connected a power supply integrated into the interface to the one or more rechargeable batteries of the coupled mobile data processing unit.

3. The portable device according to claim 1, wherein the temperature sensor has a data connection via the interface or via a Bluetooth connection to the mobile data processing unit.

4. The portable device according to claim 1, further comprising an energy accumulator arranged in the housing.

5. The portable device according to claim 4, wherein the energy accumulator comprises a small-format energy accumulator.

6. The portable device according to claim 1, wherein the heating element and the temperature sensor are connected to the mobile data processing unit via the interface with an interconnected microcontroller.

7. The portable device according to claim 6, wherein the interface is configured to transmit electrical energy and comprises a data connection to the mobile data processing unit attached in the coupled state.

8. The portable device according to claim 1, wherein the portable device is connected in the coupled state via the interface to a conventional connector of the mobile data processing unit.

9. The portable device according to claim 8, wherein the conventional connector is selected from the group consisting of a lightning connector and a USB connector.

10. The portable device according to claim 8, wherein the portable device is connected to the mobile data processing unit via Bluetooth.

11. The portable device according to claim 1, wherein the portable device is water-resistant or watertight and wherein the interface is provided with corresponding seal elements to form a watertight or water-resistant connection to the mobile data processing unit.

12. The portable device according to claim 1, wherein the control unit is configured to be provided with parameters of a heat treatment by a software application in the mobile data processing unit for operating and controlling the portable device.

13. A system with the mobile data processing unit comprising at least one of a smartphone and a tablet, and a portable device according to claim 1, wherein the mobile data processing unit is usable via a software application for operating and controlling the portable device and wherein parameters of a heat treatment are pre-determinable via the software application by corresponding inputs into the mobile data processing unit with the control unit interconnected.

14. The system according to claim 13, wherein the software application is connected to a geo-tracking function of the mobile data processing unit, and the at least one of the smartphone and the tablet is configured to place an emergency call in conjunction with a location specification can be placed either automatically upon occurrence of parameters of the emergency call predetermined in the control unit, or by a corresponding active operation of the software application.

15. The system according to claim 13, wherein the parameters of the heat treatment comprise at least one of a utilized temperature and a duration of the heat treatment.

* * * * *